United States Patent
Bui et al.

(10) Patent No.: US 9,333,161 B2
(45) Date of Patent: *May 10, 2016

(54) COMPOSITION CONTAINING AN ALKOXYSILANE AND HYALURONIC ACID

(71) Applicant: L'ORÉAL, Paris (FR)

(72) Inventors: Hy Si Bui, Piscataway, NJ (US); Anita Tong, San Francisco, CA (US); Allison Elder, North Adams, MA (US)

(73) Assignee: L'OREAL, Paris (FR)

( * ) Notice: Subject to any disclaimer, the term of this patent is extended or adjusted under 35 U.S.C. 154(b) by 344 days.

This patent is subject to a terminal disclaimer.

(21) Appl. No.: 13/922,003

(22) Filed: Jun. 19, 2013

(65) Prior Publication Data

US 2013/0280196 A1    Oct. 24, 2013

Related U.S. Application Data

(63) Continuation of application No. 12/981,867, filed on Dec. 30, 2010, now Pat. No. 8,765,110.

(51) Int. Cl.
| | |
|---|---|
| A61K 8/00 | (2006.01) |
| A61K 8/73 | (2006.01) |
| A61K 8/58 | (2006.01) |
| A61Q 19/00 | (2006.01) |
| A61Q 5/12 | (2006.01) |

(52) U.S. Cl.
CPC .................. *A61K 8/735* (2013.01); *A61K 8/585* (2013.01); *A61Q 5/12* (2013.01); *A61Q 19/00* (2013.01)

(58) Field of Classification Search
CPC ......... A61K 8/735; A61K 8/585; A61Q 5/12; A61Q 19/00
See application file for complete search history.

(56) References Cited

U.S. PATENT DOCUMENTS

| | | | |
|---|---|---|---|
| 4,824,906 A | 4/1989 | Honsberg et al. | |
| 5,891,914 A * | 4/1999 | Haney ........................... | 514/569 |
| 6,338,839 B1 | 1/2002 | Auguste et al. | |
| 2012/0171132 A1 | 7/2012 | Bui et al. | |
| 2012/0171137 A1 | 7/2012 | Bui et al. | |
| 2012/0171138 A1 | 7/2012 | Bui et al. | |
| 2012/0171139 A1 | 7/2012 | Bui et al. | |
| 2012/0171140 A1 | 7/2012 | Bui et al. | |

FOREIGN PATENT DOCUMENTS

| | | |
|---|---|---|
| BR | PI0602495 A | 2/2008 |
| EP | 2269568 A2 | 1/2011 |
| EP | 2343040 A2 | 7/2011 |
| FR | 2789896 A1 | 8/2000 |
| FR | 2926984 A1 | 8/2009 |
| JP | 2009143825 A | 7/2009 |
| WO | 0122932 A1 | 4/2001 |
| WO | 03042221 A1 | 5/2003 |

OTHER PUBLICATIONS

WIPO, International Preliminary Report, mailed on Jul. 11, 2013.
International Search Report and Written Opinion—Mailing date: Feb. 6, 2013.

* cited by examiner

*Primary Examiner* — Sreeni Padmanabhan
*Assistant Examiner* — David Browe
(74) *Attorney, Agent, or Firm* — Oblon, McClelland, Maier & Neustadt, L.L.P.

(57) ABSTRACT

A composition comprising: at least one alkoxysilane having at least one solubilizing functional group and at least one amino substituent; at least one glycosaminoglycan chosen from hyaluronic acid; water; optionally, at least one auxiliary ingredient; and optionally, at least one volatile solvent.

5 Claims, No Drawings

COMPOSITION CONTAINING AN ALKOXYSILANE AND HYALURONIC ACID

CROSS-REFERENCE TO RELATED APPLICATION

This application is a Continuation of U.S. Non-Provisional application Ser. No. 12/981,867, filed Dec. 30, 2010, which, to the extent necessary, is herein incorporated by reference.

FIELD OF THE INVENTION

The present invention relates to novel compositions and methods of making up or caring for a keratinous material. More particularly, the present invention relates to a composition which provides long-lasting moisturizing properties.

BACKGROUND OF THE INVENTION

It is well known that consumers desire to use cosmetic, personal care and dermatological products which can be employed to care for and/or enhance the appearance of keratinous materials such as skin, hair, nails and lips by providing long-lasting moisturization benefits and other beneficial properties.

Thus, there remains a need for improved compositions that would provide such benefits and which can also deliver additional benefits to keratinous materials, such as color effects, conditioning, and a soft, silky, and smooth feel to skin, hair, nails or lips.

BRIEF SUMMARY OF THE INVENTION

The present invention is directed to a composition comprising: (a) at least one alkoxysilane having at least one solubilizing functional group and at least one amino substituent; (b) at least one glycosaminoglycan chosen from hyaluronic acid; (c) water; (d) optionally, at least one auxiliary ingredient; and (e) optionally, at least one volatile solvent.

The present invention also relates to methods of moisturizing a keratinous material such as skin, hair, nails and lips comprising applying the above-described compositions onto the keratinous material.

It has been surprisingly discovered that the above-described compositions yield cosmetic compositions that impart long-lasting moisturizing properties and other benefits such as color effects, conditioning, and a soft, silky and smooth feel to skin, hair, nails and lips.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Keratinous substrates" or "keratinous material," as used herein, include but are not limited to, skin, hair and nails.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 37° C., 40° C., 45° C., 50° C., and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Long lasting" as used herein, means that the benefit provided by the composition of the present invention remains for an extended period of time from the time of application of the composition onto a keratinous material such as skin or nails or eyelashes or hair or lips.

"Moisturization" or "moisturizing" as used herein means to provide hydration or a hydrating benefit to a keratinous material such as skin or nails or eyelashes or hair or lips upon application of the composition providing such a benefit onto the keratinous material.

"Making up" as used herein means to provide decoration (for example, color) to a keratinous material such as skin or nails or eyelashes.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to nails and evaluating the color of the composition after an extended period of time. For example, the color of a composition may be evaluated immediately following application to nails and these characteristics may then be re-evaluated and compared after a certain amount of time. Further, these characteristics may be evaluated with respect to other compositions, such as commercially available compositions.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100 degrees C.

"Non-volatile", as used herein, means having a flash point of greater than about 100 degrees C.

The compositions and methods of the present invention can comprise, consist of, or consist essentially of the essential elements and limitations of the invention described herein, as well as any additional or optional ingredients, components, or limitations described herein or otherwise useful.

Alkoxysilane

According to the present invention, compositions comprising at least one alkoxysilane having at least one solubilizing functional group and amino substituent are provided. In accordance with the present invention, the alkoxysilane having at least one solubilizing functional group and amino substituent has a amine group available to react with hydrophilic groups on the backbone of the C2-C3 wax As used herein, the term "at least one solubilizing functional group" means any functional chemical group facilitating the bringing into solution of the alkoxysilane in the solvent or in a combination of solvents of the composition, for example, in solvents chosen from water, water-alcoholic mixtures, organic solvents, polar solvents and non-polar solvents.

Suitable solubilizing functional groups for use in accordance with the present disclosure include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyle, and polyether groups.

The at least one alkoxysilane present in the composition comprises at least one solubilizing functional group, which may be identical or different, such as those previously defined.

The at least one alkoxysilane having at least one solubilizing functional group and amino substituent present in the composition of the present disclosure may comprise at least one silicon atom, for example, one silicon atom.

The at least one alkoxysilane having at least one solubilizing functional group and amino substituent present in the composition may, in at least one embodiment, comprise two or three alkoxy functions. In another embodiment, the alkoxy functional groups are chosen from methoxy and ethoxy functional groups.

According to one embodiment, the at least one alkoxysilane having at least one solubilizing functional group and amino substituent present in the composition of the present disclosure is chosen from compounds of formula (I):

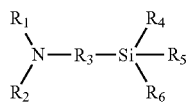

wherein:
$R_4$ is chosen from OR' groups;
$R_5$ is chosen from OR" groups;
$R_6$ is chosen from OR''' groups;
$R_1$, $R_2$ are chosen from hydrogen;
$R_3$, R', R", R''', which may be identical or different, are chosen from linear and branched, saturated and unsaturated hydrocarbon groups, optionally bearing at least one additional chemical group, wherein R', R", and R''' may also be chosen from hydrogen.

In at least one embodiment, the R', R", and R''' groups are chosen from $C_1$-$C_{12}$ alkyl, $C_6$-$C_{14}$ aryl, $C_1$-$C_8$ alkyl-$C_6$-$C_{14}$ aryl, and $C_6$-$C_{14}$ aryl-$C_1$-$C_8$-alkyl radicals.

Particularly preferred alkoxysilanes having at least one solubilizing functional group and at least one amino substituent include alkoxysilanes comprising a silicone atom. Suitable examples include those of formula R(4-n)SiXn, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Possible examples of useful alkoxysilanes include 3-mercaptopropyltriethoxysilane and aminoalkyltrialkoxysilanes such as 3-aminopropyltriethoxysilane, as described in French Patent Application No. FR 2 789 896.

In another embodiment, the useful alkoxysilanes of the present invention may be alkoxysilanes which carry a group having a cosmetic functional group, such as aromatic nitro dyes or anthraquinone, napthoquinone, benzoquinone, azo, xanthene, triarylmethane, azine, indoaniline, indophenolic or indoamine dyes; groups having a reductive effect, such as thiol groups, sulphinic acid or sulphinic salt, it being possible for these alkoxysilanes to carry a solubilizing non-hydrolysable group such as amino groups, carboxylic acids, sulphonic acids, sulphates, quaternary ammoniums, polyalcohols, polyether and phosphates. One possible example includes aminopropyl-N-(4,2-dinitrophenyl)aminopropyldiethoxysilane. Compounds of this kind are described, for example, in Patent Application EP 1 216 023.

The alkoxysilanes of the present disclosure may be amino aryl alkoxysilanes. Possible examples include but are not limited to the following compounds:

3-(m-aminophenoxy)propyltrimethoxysilane, of the formula:

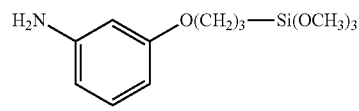

provided by GELEST,
p-aminophenyltrimethoxysilane, of formula:

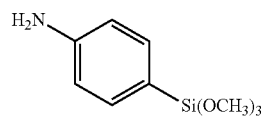

provided by GELEST, and
N-(2-aminoethylaminomethyl)phenethyltrimethoxysilane, of the formula:

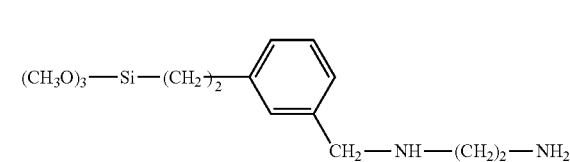

provided by GELEST.

In another embodiment the at least one alkoxysilane having at least one solubilizing functional group and at least one amino substituent is a trialkoxysilane.

In a preferred embodiment, the at least one alkoxysilane having at least one solubilizing functional group and at least one amino substituent present in the composition of the present disclosure is a γ-aminopropyltriethoxysilane, also known as 3-aminopropyltriethoxysilane.

The at least one alkoxysilane having at least one solubilizing functional group and at least one amino substituent of the present invention is soluble in both oil and water. The at least one alkoxysilane having at least one solubilizing functional group and at least one amino substituent is employed in the composition of the invention in an amount ranging from about 0.01 to about 5% by weight, such as from about 0.05 to about 3% by weight, and from about 0.1 to about 2% by weight, based on the total weight of the nail polish composition.

Glycosaminoglycan

Glycosaminoglycans (GAGs), are also referred to as acidic mucopolysaccharides on account of their high water-retaining capacity, their carbohydrate nature and their acidic nature derived from the numerous negative charges thereon. The strong anionic nature of GAGs is explained by the presence of carboxylate groups.

Suitable examples of glycosaminoglycans are hyaluronic acid or hyaluronan (HA), heparan sulfate (HS), heparin (HP), chondroitin, chondroitin sulfate (CS), chondroitin 4-sulfate or chondroitin sulfate A (CSA), chondroitin 6-sulfate or chondroitin sulfate C (CSC), dermatan sulfate or chondroitin sulfate B (CSB) and keratan sulfate (KS).

In one preferred embodiment of the present disclosure, the glycosaminoglycan is chosen from hyaluronic acid, its derivatives and its salts. In the context of the present invention, the term "hyaluronic acid or a derivative thereof/" covers the basic unit of hyaluronic acid which includes the smallest fraction of hyaluronic acid comprising a disaccharide dimer, namely D-glucuronic acid and N-acetylglucosamine.

The term "hyaluronic acid or a derivative thereof" also comprises, in the context of the present invention, the linear polymer comprising the polymeric unit described above, linked together in the chain via alternating beta(1,4) and beta(1,3) glycosidic linkages, having a molecular weight (MW) that can range between 380 and 13,000,000 daltons (Da). This molecular weight depends in large part on the source from which the hyaluronic acid is obtained and/or on the preparation methods.

The term "hyaluronic acid or a derivative thereof" also comprises, in the context of the present invention, the hyaluronic acid salts, and in particular the alkali metals salts such as the sodium salt and the potassium salt.

In the natural state, hyaluronic acid is present in pericellular gels, in the base substance of the connective tissues of vertebrate organs such as the dermis and epithelial tissues, and in particular in the epidermis, in the synovial fluid of the joints, in the vitreous humor, in the human umbilical cord and in the crista galli apophysis.

Thus, the term "hyaluronic acid or a derivative thereof" comprises all the fractions or subunits of hyaluronic acid having a molecular weight in particular within the molecular weight range recalled above.

According to a preferred embodiment of the invention the hyaluronic acid fractions suitable for the use covered by the present invention have a molecular weight of between 50,000 and 5,000,000, in particular between 100,000 and 5,000,000, especially between 400,000 and 5,000,000 Da. In this case, the term used is high-molecular-weight hyaluronic acid.

Alternatively, the hyaluronic acid fractions that may also be suitable for the use in the present invention are chosen from those with a molecular weight of between 50,000 and 400,000 Da (intermediate-molecular-weight hyaluronic acid) and from those with a molecular weight of less than 50,000 Da (low-molecular-weight hyaluronic acid).

Finally, the term "hyaluronic acid or a derivative thereof" also comprises hyaluronic acid esters in particular those in which all or some of the carboxylic groups of the acid functions are esterified with oxyethylenated alkyls or alcohols, containing from 1 to 20 carbon atoms, in particular with a degree of substitution at the level of the D-glucuronic acid of the hyaluronic acid ranging from 0.5 to 50 percent. Mention may in particular be made of methyl, ethyl, n-propyl, n-pentyl, benzyl and dodecyl esters of hyaluronic acid.

The molecular weights indicated above are also valid for the hyaluronic acid esters.

Hyaluronic acid may in particular be hyaluronic acid supplied by the company Hyactive under the trade name CPN (MW: to 150 kDa), by the company Soliance under the trade name Cristalhyal (MW: 1.1 million Da), by the company Bioland under the name Nutra HA (MW: 820,000 Da), by the company Bioland under the name Nutra AF (MW: 69,000 Da, by the company Bioland under the name Oligo HA (MW: 6100 Da) or else by the company Vam Farmacos Metica under the name D Factor (MW: 380 Da).

In one embodiment, the hyaluronic acid is present in the form of spheres. In particular, such spheres are sold by the company BASF under the name Sphere d'Acide Hyaluronique [hyaluronic acid sphere]. It is a mixture of hyaluronic acid of various molecular weights, i.e. of MW 1.5 million, 400,000 and 600,000 Da.

The preferred form of hyaluronic acid in the present invention is sodium hyaluronate, which is commercially available from Soliance in three different forms produced from the fermentation of lactic bacteria on a plant substrate and known under the tradenames Bashyal, Vitalhyal and Cristalhyal, whose molecular weights range from less than 0.2 million Da to more than 1 million Da.

Preferably, the at least one glycosaminoglycan chosen from hyaluronic acid is employed in the compositions of the present invention in an amount of from about 0.01% to about 5% by weight, more preferably, from about 0.2% to about 2.0% by weight, and more preferably, from about 0.5% to about 1.5% by weight with respect to the total weight of the composition, including all ranges and subranges therebetween.

Water

The composition of the present invention comprises water. In accordance with preferred embodiments, water is preferably present in the composition in an amount of from about 10% to about 99.98% by weight, preferably from about 12% to about 99.5% by weight, preferably from about 15 to about 99% by weight, including all ranges and subranges therebetween, all weights based on the total weight of the composition.

Volatile Solvent

The composition of the present invention may further comprise at least one volatile solvent. Examples of such volatile solvents include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other preferred embodiments, the volatile solvent may be chosen from one or more non-silicone volatile oils and may be selected from volatile alcohols, hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
| --- | --- |
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

In the event that a volatile solvent is present in the composition of the present invention, the volatile solvent may be employed in an amount of from about 1% to about 75% by weight, such as from about 10% to about 60% by weight, such as from about 15 to about 55% by weight, including all ranges and subranges therebetween, all weights based on the total weight of the composition.

In certain embodiments of the present invention, when a volatile solvent is employed, the alkoxysilane having at least one solubilizing functional group and at least one amino substituent may initially be present in the volatile solvent and the glycosaminoglycan chosen from hyaluronic acid may initially be present in water. In one preferred embodiment, the combination of the volatile solvent containing the alkoxysilane with the water containing the glycosaminoglycan chosen from hyaluronic acid results in the formation of an emulsion.

Although not wanting to be bound by any particular theory, it is also believed that a physical interaction (non-covalent bonding) occurs between the alkoxysilane having at least one solubilizing functional group and at least one amino substituent and the glycosaminoglycan chosen from hyaluronic acid resulting in the production of a flexible and/or elastic hydrating film. The resultant composition is eminently capable of forming a film. Moreover, the composition is stable, imparts long-lasting moisturization due to the entrapment of water therein, and can carry various types of desired ingredients.

Auxiliary Ingredient

The composition of the present invention may also comprise at least one auxiliary ingredient commonly used in cosmetic, personal care, and topical compositions and known to a person skilled in the art as being capable of being incorporated into such compositions. Such auxiliary ingredients may be chosen from surfactants, pigments, colorants, moisturizing agents, thickeners, coalescents, preservatives, fragrances, natural and synthetic oils, waxes, antioxidants, agents for combating free radicals, spreading agents, wetting agents, dispersing agents, antifoaming agents, neutralizing agents, stabilizing agents, skin active agents, UV screening agents, sunscreens, vitamins, proteins, ceramides, plant extracts, fibers, pharmacologically active agents, dermatologically active agents, and their mixtures.

According to other particularly preferred embodiments of the present invention, the auxiliary ingredient can also chosen from at least one colorant and/or at least one pigment. Any colorant typically found in cosmetic compositions can be used. Suitable colorants include, but are not limited to, lipophilic dyes, pigments and pearlescent agents, and their mixtures.

Suitable examples of fat-soluble dyes are, for example, Sudan red, DC Red 17, DC Green β-carotene, soybean oil, Sudan brown, DC Yellow 11, DC Violet 2, DC Orange 5 and quinoline yellow.

Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescent pigments can be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

In accordance with preferred embodiments, the at least one colorant and/or pigment, if present, is preferably present in the composition in an amount of from about 0.01% to about 20% by weight, preferably from about 0.1% to about 15% by weight, preferably from about 0.5 to about 10% by weight, including all ranges and subranges therebetween, all weights based on the total weight of the composition.

Needless to say, the composition of the invention should be cosmetically or dermatologically or pharmacologically acceptable, i.e., it should contain non-toxic physiologically acceptable components. The composition may be in any galenic form normally employed in the cosmetic, personal care, dermatological and pharmacological fields which is suitable for topical administration onto keratinous materials such as skin, hair, nails and lips.

It has been surprisingly and unexpectedly discovered that the combination of the alkoxysilane having at least one solubilizing functional group and at least one amino substituent with a glycosaminoglycan chosen from hyaluronic acid results in the formation of a composition having long-lasting moisturizing properties.

According to other preferred embodiments of the present invention, methods of making up or caring for a keratinous material such as skin, comprising applying the composition of the present invention to the keratinous material in an amount sufficient to make up or care for the keratinous material, are provided. The compositions according to the invention can be manufactured by known processes used generally in the cosmetics or dermatological field.

The compositions described above are useful as compositions for making up, caring for, and conditioning keratinous materials. These compositions include skin care and sun care products such as moisturizers, lotions, facial masks, and sunscreens, personal hygiene products, and lip and nail care products, makeup products such as lipsticks, nail polishes, eyeshadow, foundation and mascara, hair products such as styling and hair conditioning products.

The compositions of the present invention are also useful as a prephase composition for incorporation into a final composition or as a thickener or rheology modifier.

Having described the subject matter of the present disclosure by way of illustration and example for purposes of clarity of understanding, it will be apparent to one of ordinary skill in the art that the same can be performed by modifying or changing the subject matter within a variety of conditions, formulations and other parameters without affecting its scope or any specific embodiment thereof, and that such modifications or changes are intended to be encompassed within the scope of the appended claims.

The following examples are for illustrative purposes only and are not intended to limit the scope of the claims.

EXAMPLES

| Chemical Name | Comparative Example 1 | Inventive Example 2 | Inventive Example 3 |
|---|---|---|---|
| Deionized Water | 99.00 | 98.00 | 97.00 |
| Sodium Hyaluronate | 1.00 | 1.00 | 1.00 |
| Aminopropyl Triethoxysilane | 0.00 | 1.00 | 2.00 |

Procedure

Sodium Hyaluronate was completely swelled in deionized water for at least 8 hours at room temperature. Aminopropyl Triethoxylsilane was slowly added to the mixture with moderate agitation of about 200 rpm. The mixture was mixed for 8-24 hrs.

The compositions in the table above were applied onto a substrate and the resulting films were allowed to dry for 2 days under ambient conditions. Each film was then tested for water resistancy by applying a drop of water to the film and then noting the length of time it took for the film to dissolve.

Comparative example 1 formed a gel. The dried film was found to be brittle and not water resistant, that is, the film dissolved instantaneously when a drop of water was placed on the film.

Inventive Example 2 formed a gel. The dried film was found to be significantly more elastic and surprisingly water resistant in contrast to comparative example 1, that is it took longer for the film to dissolve when a drop of water was placed on the film.

Inventive Example 3 formed a gel. The dried film was found to be significantly even more elastic and surprisingly more water resistant compared to inventive example 2, that is it took even longer for the film to dissolve when a drop of water was placed on the film.

Water resistance of the film indicates that the film has retained water therein which, consequently, enables the film to continue to moisturize the keratinous substrate onto which it has been applied.

What is claimed is:

1. A method of moisturizing a keratinous material comprising applying onto the keratinous material an aqueous composition comprising:
    (a) at least one alkoxysilane having at least one solubilizing functional group and at least one amino substituent, said alkoxysilane being present in an amount of from about 0.01% to about 5% by weight, based on the total weight of the composition;
    (b) at least one glycosaminoglycan chosen from hyaluronic acid, said glycosaminoglycan being present in an amount of from about 0.01% to about 5% by weight, based on the total weight of the composition;
    (c) water present in an amount of from about 12% to about 99.5% by weight, based on the total weight of the composition;
    (d) optionally, at least one auxiliary ingredient; and
    (e) optionally, at least one volatile solvent;
    wherein component (a) is solubilized in component (c) or in a combination of components (b) and (c) prior to application of the composition onto the keratinous material, and
    wherein the aqueous composition is a gel composition made by mixing components (a), (b) and (c) for at least 8 hours.

2. The method of claim 1, wherein component (a) includes 3 aminopropyltriethoxysilane.

3. The method of claim 2, wherein component (d) includes at least one colorant or pigment.

4. The method of claim 2, wherein component (e) is present in an amount of from about 1 to about 75% by weight, based on the total weight of the composition.

5. A method of moisturizing a keratinous material comprising applying onto the keratinous material an aqueous composition comprising:
    (a) from about 0.1 to about 2% of at least one alkoxysilane having at least one solubilizing functional group and at least one amino substituent and including 3-aminopropyltriethoxysilane;
    (b) from about 0.5 to about 1.5% by weight of at least one glycosaminoglycan chosen from hyaluronic acid;
    (c) from about 12% to about 99.5% by weight water; (d) optionally, at least one auxiliary ingredient; and
    (e) optionally, at least one volatile solvent; all weights being based on the total weight of the composition; and
    wherein component (a) is solubilized in component (c) or in a combination of components (b) and (c) prior to application of the composition onto a keratinous material, and wherein the aqueous composition is a gel composition made by mixing components (a), (b) and (c) for at least 8 hours.

* * * * *